US009427718B2

(12) United States Patent
Dubois et al.

(10) Patent No.: US 9,427,718 B2
(45) Date of Patent: Aug. 30, 2016

(54) CONTINUOUS CATALYST REGENERATION IN A FLUIDIZED BED REACTOR

(75) Inventors: Jean-Luc Dubois, Millery (FR); Grégory Patience, Québec (CA)

(73) Assignee: ARKEMA FRANCE, Colombes (FR)

( * ) Notice: Subject to any disclaimer, the term of this patent is extended or adjusted under 35 U.S.C. 154(b) by 70 days.

(21) Appl. No.: 14/232,476

(22) PCT Filed: Jul. 9, 2012

(86) PCT No.: PCT/FR2012/051617
§ 371 (c)(1),
(2), (4) Date: Jan. 13, 2014

(87) PCT Pub. No.: WO2013/007941
PCT Pub. Date: Jan. 17, 2013

(65) Prior Publication Data
US 2014/0171685 A1     Jun. 19, 2014

(30) Foreign Application Priority Data

Jul. 12, 2011   (FR) ...................................... 11 56312

(51) Int. Cl.
*C07C 51/377*     (2006.01)
*B01J 8/24*       (2006.01)
(Continued)

(52) U.S. Cl.
CPC ................ *B01J 8/24* (2013.01); *B01J 8/0055* (2013.01); *B01J 8/1818* (2013.01); *B01J 8/1827* (2013.01); *B01J 8/1836* (2013.01); *B01J 8/226* (2013.01); *B01J 8/386* (2013.01); *B01J 23/92* (2013.01); *B01J 27/285* (2013.01); *B01J 38/30* (2013.01); *C07C 45/38* (2013.01); *C07C 45/52* (2013.01);
(Continued)

(58) Field of Classification Search
None
See application file for complete search history.

(56) References Cited

U.S. PATENT DOCUMENTS

| 2,698,281 A | 12/1954 | Leffer |
| 2,872,472 A | 2/1959 | Fenske et al. |

(Continued)

FOREIGN PATENT DOCUMENTS

| DE | 102008038273 | * | 3/2010 |
| EP | 0 340 852 A2 | | 11/1989 |

(Continued)

OTHER PUBLICATIONS

Machine Translation of DE 102008038273.*

(Continued)

*Primary Examiner* — Karl J Puttlitz
(74) *Attorney, Agent, or Firm* — Buchanan Ingersoll & Rooney P.C.

(57) ABSTRACT

A catalytic reactor including a chamber (1) and separation means (2) arranged inside the chamber (1), said separation means defining at least one reaction area (3) and at least one regeneration area (4), the reaction area (3) being supplied with a reaction flow (15, 16) and connected, at the outlet thereof, to a first gas tapping device (13), the regeneration area (4) being supplied with a regeneration flow (17) and connected, at the outlet thereof, to a second gas tapping device (10), the reactor being suitable for including a fluidized bed of catalyst particles (5) in the reaction area (3), the separation means (2) enabling the catalyst particles to pass from the reaction area (3) to the regeneration area (4), and the reactor making it possible to move catalyst particles into the regeneration area (4) so as to enable the return thereof to the reaction area (3).

5 Claims, 1 Drawing Sheet

(51) Int. Cl.
*B01J 8/00* (2006.01)
*B01J 8/18* (2006.01)
*B01J 8/22* (2006.01)
*B01J 8/38* (2006.01)
*B01J 38/30* (2006.01)
*B01J 23/92* (2006.01)
*B01J 27/28* (2006.01)
*C07C 45/38* (2006.01)
*C07C 45/52* (2006.01)
*C07C 51/215* (2006.01)
*C07C 51/235* (2006.01)
*C07C 51/265* (2006.01)
*C07C 51/31* (2006.01)

(52) U.S. Cl.
CPC .......... *C07C 51/215* (2013.01); *C07C 51/235* (2013.01); *C07C 51/265* (2013.01); *C07C 51/313* (2013.01); *C07C 51/377* (2013.01); *B01J 2208/0084* (2013.01); *B01J 2208/00141* (2013.01); *B01J 2208/00203* (2013.01); *B01J 2208/00557* (2013.01); *Y02P 20/584* (2015.11)

(56) References Cited

U.S. PATENT DOCUMENTS

| | | |
|---|---|---|
| 3,057,923 A | 10/1962 | Hellin |
| 3,669,877 A | 6/1972 | Friedrich |
| 4,623,443 A | 11/1986 | Washer |
| 6,437,208 B1 | 8/2002 | Kuechler et al. |
| 2003/0073751 A1 | 4/2003 | Culross |
| 2007/0203383 A1 | 8/2007 | Bozzano et al. |
| 2010/0028224 A1 | 2/2010 | Miller |
| 2010/0106090 A1 | 4/2010 | Matusch |
| 2010/0204502 A1* | 8/2010 | Dubois .................. 558/315 |
| 2011/0028760 A1 | 2/2011 | Dubois et al. |
| 2011/0071322 A1 | 3/2011 | Dubois |

FOREIGN PATENT DOCUMENTS

| | | |
|---|---|---|
| EP | 1 848 681 B1 | 7/2008 |
| FR | 2 920 767 A1 | 3/2009 |
| WO | WO 2009/012855 A1 | 1/2009 |
| WO | WO 2009/044081 A1 | 4/2009 |
| WO | WO 2009/156655 A1 | 12/2009 |
| WO | WO 2010/046227 A1 | 4/2010 |

OTHER PUBLICATIONS

Zhang et al., Chem. Eng. Technol. 2009, 32, No. 1, 27-37.*
Machine Translation of DE 102008038273 Mar. 2010.*
International Search Report (PCT/ISA/210) mailed on Jan. 23, 2013, by the French Patent Office as the International Searching Authority for International Application No. PCT/FR2012/051617.
Zhang et al., "Hydrodynamics of a novel biomass autothermal fast pyrolysis reactor: flow pattern and pressure drop", Chem. Eng. Technol., 2009 (month unknown), pp. 27-37, vol. 32, No. 1.

* cited by examiner

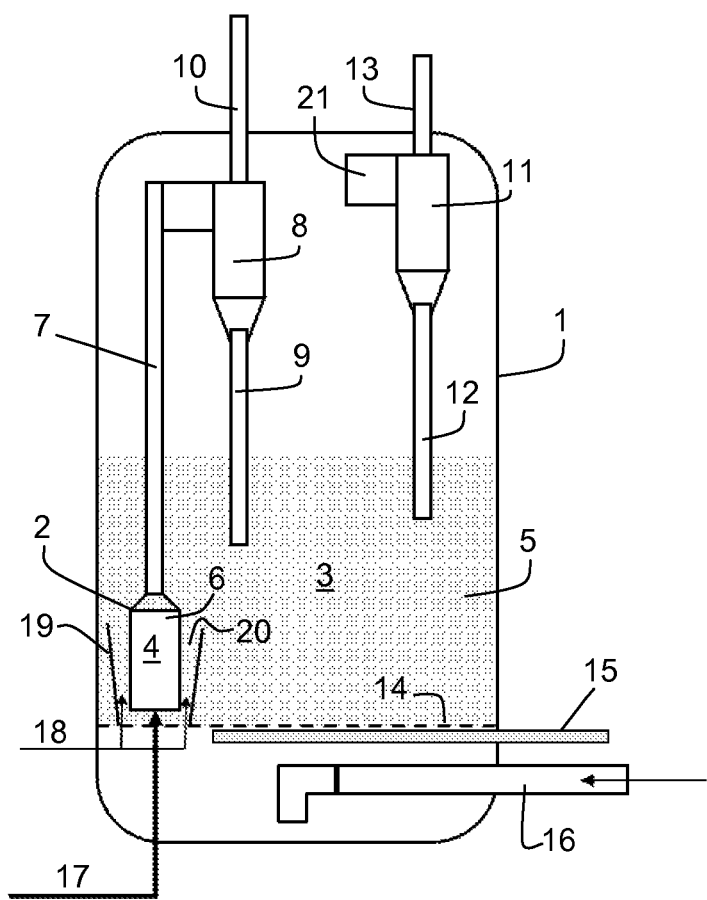

CONTINUOUS CATALYST REGENERATION IN A FLUIDIZED BED REACTOR

FIELD OF THE INVENTION

The present invention provides a catalytic reactor in which the catalyst is regenerated continuously in the chamber of the reactor itself. This catalytic reactor is suitable for the implementation of a large number of chemical reactions.

TECHNICAL BACKGROUND

The use of catalytic fluidized bed reactors is known in processes of chemical engineering.

Also known is the placement of an aspiration tube in the chamber of a fluidized bed reactor, to promote the circulation of the solid species within the reactor (ICFB reactors).

Likewise known is the combination of the catalytic reactor with a regenerator disposed adjacent to it, and the establishment of a spent catalyst stream from the reactor to the regenerator, and of a regenerated catalyst stream from the regenerator to the reactor. Systems of this kind are appropriate when the deactivation of the catalyst is relatively rapid (typically over a period of the order of a few seconds or minutes) and the catalyst requires frequent regeneration. These systems are used in particular for the conversion of hydrocarbons to oxygen-containing olefins. Examples of these systems are provided by documents U.S. Pat. No. 6,437,208, US 2007/0203383, and US 2010/0028224.

The Zhang et al. article titled *Hydrodynamics of a novel biomass autothermal fast pyrolysis reactor: flow pattern and pressure drop*, in Chem. Eng. Technol. 32:27-37 (2009), describes a reactor for the catalytic pyrolysis of biomass, in which the pyrolysis is carried out in a central part, with entrainment of biomass and of catalyst, while the deposits on the catalyst are burnt in a peripheral zone of the reactor. This reactor design, however, is not suitable for reactions where the residence time of the catalyst in the reaction zone has to be relatively high (of the order of several hours, for example) for the purpose of optimum efficiency.

The catalytic fluidized bed reactors of the prior art are not suitable for allowing effective control of the reaction gas flow rate independently from the stream of catalyst for regeneration, or for effectively providing the regenerator with heat, in order to optimize the implementation of chemical reactions in the gas phase (U.S. Pat. Nos. 4,623,443; 3,057,923; US 2003/073751; U.S. Pat. No. 2,872,472; EP 340 852).

At the present time there is no facility that is sufficiently compact and allows optimum control of the operating conditions, especially for reactions in which the deactivation of the catalyst has a characteristic duration with an order of magnitude of greater than a minute and less than a month.

SUMMARY OF THE INVENTION

The invention pertains firstly to a catalytic reactor comprising a chamber and separating means disposed in the chamber, delimiting at least one reaction zone and at least one regeneration zone, the reaction zone being supplied by a reaction stream feed device and being outlet-connected to a first gas withdrawal device, the regeneration zone being fed by a regeneration stream feed device and being outlet-connected to a second gas withdrawal device, the reactor comprising a fluidized bed of catalyst particles in the reaction zone, the separation means allowing the passage of the catalyst particles from the reaction zone to the regeneration zone, and the reactor being suitable for including entrainment of catalyst particles into the regeneration zone that allows them to return to the reaction zone.

The reactor according to the invention is characterized in that the ratio of the maximum cross section of catalyst bed in the reaction zone to the maximum cross section of the regeneration zone (or zones), taken collectively, is from 1 to 100, preferably from 5 to 50.

According to one embodiment, the separating means comprise a tubular wall, the reaction zone is situated outside the tubular wall, and the regeneration zone is situated inside the tubular wall.

According to one embodiment, the ratio of the maximum cross section of catalyst bed in the reaction zone to the maximum cross section of the regeneration zone (or zones), taken collectively, is more particularly from 10 to 20.

According to one embodiment, the regeneration zone comprises a top part and a bottom part, the top part having a cross section lower than that of the bottom part, the bottom part being suitable for including a fluidized bed of catalyst particles, and the top part being suitable for entraining the catalyst particles.

According to one embodiment, the catalytic reactor comprises a lower grid in the chamber, suitable for retaining the catalyst particles above it, and a clearance is made between the separating means and the lower grid, allowing the passage of the catalyst particles from the reaction zone to the regeneration zone.

According to one embodiment, the catalytic reactor comprises a baffle system in the reaction zone making a space between the baffle system and the separating means.

According to one embodiment, the catalytic reactor comprises means for injecting backpressure gas into the space.

The invention likewise pertains to a chemical reaction process comprising concomitantly:
  feeding by a reaction stream of a fluidized bed of catalyst particles into a reaction zone disposed in a chamber of a reactor,
  withdrawing a stream comprising reaction products at the outlet of the reaction zone,
  passing, using separating means, catalyst particles from the reaction zone to a regeneration zone disposed inside the chamber of the reactor,
  feeding the regeneration zone by a regeneration stream,
  regenerating the catalyst particles and pneumatically entraining the catalyst particles into the regeneration zone,
  withdrawing an exhaust gas at the outlet of the regeneration zone, and
  returning the entrained catalyst particles to the reaction zone.

According to one embodiment, the gas feed in the top part of the regenerator (riser) is independent of the gas feed in the lower part of the regenerator, thus enabling more effective control of the head loss and hence of the circulating solid flow rate.

According to the invention, said chemical reaction is characterized in that the deactivation time of the catalyst is from 1 to 20 times greater than the regeneration time.

According to one embodiment, the stream of catalyst particles from the reaction zone to the regeneration zone is regulated by the injection of a backpressure gas.

According to one embodiment, the regeneration stream comprises oxygen, and preferably the reaction stream comprises oxygen.

According to one embodiment, the process is:
a process for dehydrating glycerol to acrolein; or
a process for dehydrating lactic acid to acrylic acid; or
a process for dehydrating 3-hydroxypropionic acid to acrylic acid; or
a process for dehydrating 3-hydroxyisobutyric acid to methacrylic acid; or
a process for dehydrating 2-hydroxyisobutyric acid, also called alpha-hydroxyisobutyric acid, to methacrylic acid.

According to one embodiment, the process is implemented in a catalytic reactor as described above.

With the present invention it is possible to overcome the drawbacks in the prior art. The invention provides more particularly a compact reactor facility which allows optimum control of the operating conditions. The invention is particularly useful for reactions in which the deactivation of the catalyst takes a characteristic time with an order of magnitude greater than a minute and less than a month; and/or for reactions in which the deactivation time (defined as being the reaction time after which the catalyst has lost 25% of its efficiency) is from 1 to 20 times, preferably from 1 to 10 times, more than the regeneration time (defined as being the regeneration time after which a catalyst that has lost 25% of its initial efficacy regains up to about 100% of said initial efficacy).

This is accomplished by virtue of a reactor model in which the regeneration of the catalyst takes place actually inside the reactor, in a dedicated regeneration zone, this regeneration zone operating in a regime of entrainment of the catalyst particles.

According to certain particular embodiments, the invention also has one or, preferably, two or more of the advantageous characteristics set out hereinbelow:

In the customary fluidized beds comprising internal circulation means such as an aspiration tube, the head loss in the aspiration tube is controlled by the gas flow rate. Any increase in the gas flow rate also brings about an increase in the catalyst stream and hence a reduction in the residence time of the catalyst. Owing to this interaction between gas flow rate and flow of catalyst, the design of these reactors is particularly complex. The invention, on the other hand, according to one embodiment, envisages the injection of a backpressure gas at the junction between the reaction zone and the regeneration zone. This enables the catalyst stream to be controlled independently of the gas flow rate, and hence allows a high catalyst residence time to be maintained. In other words, the invention allows more effective control of the hydrodynamics, particularly in the regeneration zone, thereby simplifying the design of the reactor.

The invention makes it possible to separate the gases from the reaction zone and from the regeneration zone, and thereby, in particular, to avoid mixtures of oxygen and hydrocarbons that may give rise to risks of explosion, combustion, or partial or complete oxidation.

The injection of backpressure gas makes it possible to limit the passage to the regeneration zone of circulating gas in the reaction zone, and thereby to limit the losses of reactants or of reaction products.

BRIEF DESCRIPTION OF THE FIGURES

FIG. 1 represents schematically one embodiment of a reactor according to the invention, in section.

DESCRIPTION OF EMBODIMENTS OF THE INVENTION

The invention is now described in more detail and non-limitatively in the description which follows.

Reactor

With reference to FIG. 1, the catalytic reactor according to the invention comprises a chamber 1. The chamber 1 may have a shape which is cylindrical overall with a circular cross section, or cylindrical overall with a square or rectangular, or more generally polygonal, cross section. The principal axis of the chamber (axis of the cylinder) is preferably disposed in the vertical direction, as illustrated. The reactor operates preferably in ascending flow, meaning that the reactor is fed with reactants at the bottom and that the products of the reaction are taken off at the top of the reactor.

According to certain embodiments (not shown), the chamber 1 may include a form which is tubular overall on the vertical axis, with a variable cross section. For example, a top part of the reactor may have a cross section greater than a bottom part of the reactor. In this case, the top part constitutes a release zone of the reactor, thereby limiting the entrainment of solid particles into the top part of the reactor.

Inside the chamber 1, separating means 2 delimit a reaction zone 3 and a regeneration zone 4. The separating means 2 generally comprise a separating wall or a plurality of separating walls. In the embodiment illustrated, the separating means 2 consist of a tubular separating wall with a circular cross section. Alternatively, an assembly of separating walls forming a tube having a rectangular or square, or more generally polygonal, cross section may be used. The reaction zone 3 is preferably situated outside the tubular wall or walls, and the regeneration zone 4 is situated inside.

Alternatively it is possible to use one or more separating walls forming a tube conjointly with a part of the chamber 1. In that case, the regeneration zone is delimited both by a part of the chamber 1 and by the separating walls.

In the embodiment illustrated, the regeneration zone 4 is arranged eccentrically relative to the principal axis of the chamber 1. For reasons of flow symmetry, however, it is preferable to dispose the regeneration zone 4, when it is the sole such zone, in a central position within the chamber 1.

It is also possible to provide a plurality of regeneration zones 4, each being provided with distinct separating means 2, within the chamber 1. In this case, a symmetrical or regular arrangement of the different regeneration zones 4 relative to the principal axis of the chamber 1 is preferred. A plurality of regeneration zones 4 makes it easier to extrapolate between different sizes of units, while retaining the identically sized regeneration zones 4.

A catalyst in the form of solid particles is disposed in the chamber 1. The separating means 2 are provided in such a way that there is communication between the reaction zone 3 and the regeneration zone 4 for the catalyst to circulate from the reaction zone 3 to the regeneration zone 4.

In the embodiment illustrated, the catalyst is present in the reaction zone 3 in the form of a fluidized bed 5 above a lower grid 14 (the size of whose orifices is suitable for retaining the catalyst particles). A reaction stream feed device 15, 16 feeds the catalyst bed 5 with fluid. This device comprises at least means 16 for injecting fluidizing gas under the lower grid 14. The fluidizing gas is a gas with a flow rate adapted such that the catalyst bed 5 is in fluidized form.

In the embodiment illustrated, the means 16 for injecting fluidizing gas are oriented downward, such that the fluidizing gas is injected toward the bottom of the chamber 1, where it is directed upward, and passes through the lower grid 14 and then through the catalyst bed 5. This permits a more uniform feed of fluidizing gas. Alternatively, provision may also be made for the fluidizing gas injection means 16 to be oriented directly upward, in other words toward the catalyst bed 5.

The reaction stream feed device 15, 16 may also, furthermore, comprise complementary feed means 15, as is illustrated. The complementary feed means 15 may be disposed under the lower grid 14, vertically within the reaction zone 3, as illustrated. The lower grid 14 may then act as a distributing grid.

Alternatively, provision may be made for the complementary feed means 15 to be disposed above the lower grid 14, in other words to open out directly into the catalyst bed 5, either at a single vertical side or in a staged fashion at a number of levels in the catalyst bed 5.

It is also possible to carry out staged feeding both above and below the lower grid 14.

The complementary feed means 15 may comprise an assembly of injection ducts equipped with orifices, arranged for example in concentric circles, or else has a network of parallel lines.

The "reaction stream" is the whole of the compounds feeding the reaction zone 3. This reaction stream comprises the reactants, optionally inert compounds, and optionally one or more substances for regenerating the catalyst, as for example an oxidizing compound (and in particular oxygen) in order to extend the deactivation time of the catalyst. The reaction stream may be purely gaseous or may comprise gas and liquid. In this latter case, the liquid is vaporized in situ in the chamber 1.

The reaction stream is introduced either wholly by the fluidizing gas injection means 16, or partly by said means and partly by the complementary feed means 15, when the latter are present.

For example, if oxygen is injected as part of the reaction stream, it may be appropriate to introduce it separately from the hydrocarbon reactants, and to introduce it directly into the catalyst bed 5, in order to prevent any explosion risk. It may also be opportune to inject it in a staged manner at a number of levels in the catalyst bed 5 for more effective control of the temperature and/or flammability. If one or more compounds forming part of the reaction stream are injected in liquid form, it may be appropriate to introduce them directly into the catalyst bed 5 (using complementary feed means 15) to bring about immediate vaporization thereof on contact with the solid.

This is of advantage in particular for thermally unstable compounds (glycerol, lactic acid, etc.), which have a tendency to break down at a temperature lower than their boiling point. The reason is that in this case the travel time of these compounds at high temperature is minimized, and they are reacted simultaneously with their temperature increase and vaporization (since the heat transfer within the catalyst bed is very efficient, owing to the presence of solid particles).

On the other hand, injection below the lower grid 14 is preferred for thermally stable compounds.

Injection directly into the catalyst bed 5 is also appropriate for liquids which may crystallize or contain salts. Owing to the mechanical forces of attrition between the grains of catalyst, the solid particles which would form are, in fact, destroyed in this way and removed from the reactor.

The regeneration zone 4 comprises a bottom part 6 and a top part 7, with the top part 7 generally having a cross section less than the lower part 6.

In the lower part 6, the catalyst is present in the form of a fluidized bed. The top part 7 may be termed an elevating part, meaning that the catalyst is entrained (upwardly) therein by pneumatic transport. To put it another way, the linear velocity of the gas in this top part 7 is greater than the limiting velocity of free fall of the catalyst particles.

A regeneration stream feed device 17 allows the regeneration zone 4 to be fed specifically with regeneration stream, on or below the lower grid 14.

The regeneration stream may be purely gaseous or may comprise a liquid component, and is preferably purely gaseous. It comprises a regenerating substance, in other words a substance suitable for regenerating the catalyst, being identical or different from the regenerating substance optionally employed in the reaction zone 3, and being preferably an oxidizing substance such as oxygen; and it optionally comprises one or more inert compounds.

A regeneration stream containing oxygen is appropriate in particular for catalysts which are deactivated by coking, since it allows combustion of the coke. The regeneration stream preferably comprises oxygen and one or more inert heat-transfer compounds (nitrogen, water vapor, carbon dioxide, etc.). For example, the regeneration stream is air.

The flow rate of the regeneration stream is adapted such that the fluidized bed in the bottom part 6 of the reaction zone 4 is a rapid fluidized bed; the linear velocity of the gas therein is preferably higher than in the catalyst bed 5 of the reaction zone 3.

The residence time of the catalyst particles in the bottom part 6 of the regeneration zone 4 is largely greater than the residence time of the catalyst particles in the top part 7 of the regeneration zone 4; the essential part of regeneration therefore takes place in the bottom part 6. Generally speaking, the regeneration of the catalyst in the regeneration zone 4 is not complete; it is adjusted to maintain a predetermined average degree of activation of the catalyst throughout the reaction zone 3.

The catalyst particles are entrained by pneumatic transport from the upper end of the bottom part 6 of the regeneration zone 4, from bottom to top along the top part 7 of the regeneration zone 4, until they reach a first gas/solid separation device 8.

The first gas/solid separation device 8 may be a cyclonic separator. It is outlet-connected on the one hand to a first gas withdrawal device 10, which evacuates the exhaust gases from the regeneration, and on the other hand to first catalyst return means 9, for example a return leg, which returns the catalyst to the reaction zone 3.

In the top part of the reaction zone 3 there is provided a second gas/solid separation device 11, preferably a cyclonic separator. It is provided with an entry port 21 and is outlet-connected on the one hand to a second gas withdrawal device 13, which evacuates a stream comprising the reaction products, and on the other hand to second catalyst particle return means 12, as for example a return leg, which returns the catalyst to the reaction zone 3.

It is also possible for a plurality of such gas/solid separation devices to be provided in the reaction zone 3.

In order to allow the passage of the catalyst from the reaction zone 3 to the regeneration zone 4, the separating wall 2 does not make contact with the lower grid 14; instead, a clearance is made between the bottom part of the separating wall 2 and the lower grid 14.

In the embodiment illustrated, a baffle system 19 is provided in the reaction zone 3, making a space 20 between the separating wall 2 and the baffle system 19. When the separating wall 2 is tubular, the baffle system 19 surrounds the separating wall 2 (in a portion lower than the latter) at a distance from it. The baffle system 19 may have a tubular form parallel to the separating wall 2, or else, as illustrated, it may be widened toward the top: in this way, the velocity of the catalyst particles in the space 20 decreases as they travel downward, and the gas bubbles are therefore better able to escape to the rest of the reaction zone 3, thereby minimizing the entrainment of gas toward the regeneration zone 4.

Backpressure injection means 18 are provided advantageously. They are suitable for injecting a gas into the space 20. In this way it is possible to regulate the flow of catalyst from the reaction zone 3 to the regeneration zone 4 independently of the flow rate of regeneration stream in the regeneration zone 4, and the passage of the reaction stream into the regeneration zone 4 is blocked.

The gas injected into the intermediate zone 20 is preferably a chemically inert gas. This makes it possible advantageously to "strip" the catalyst (in other words, to carry out partial desorption of all of the reactants adsorbed on the catalyst, but in particular to substitute the reactant-rich gas contained in and present around the catalyst particles), so as to limit the entrainment of reactants to the regeneration zone 4. This gas may in particular be nitrogen, $CO_2$, water vapor, a mixture of these gases, or else the recycled gas, obtained upstream of the process, containing primarily gases purged from the main product of the reaction carried out in the reactor. The gas is preferably rich in water vapor, in $CO_2$, or in nitrogen. More preferably, the gas is water vapor.

A heat exchange system, not shown, comprising, for example, cooling pins, may be provided in and/or around the chamber 1. It is also possible to provide cooling specifically for the reaction zone 3 and/or the regeneration zone 4 (on the understanding that the regeneration temperature is generally higher than the reaction temperature).

The ratio of the maximum cross section of catalyst bed 5 in the reaction zone 3 to the maximum cross section of the regeneration zone 4 (in other words, the cross section of its bottom part 6, in the example illustrated in which this bottom part 6 is cylindrical) or of the regeneration zones (where there are two or more) is greater than or equal to 1 and less than 100; preferably it is from 5 to 50, and more particularly from 10 to 20. Such sizing minimizes the reactor volume dedicated to regeneration, and results in optimum efficiency.

The catalytic reactor according to the invention is advantageously suitable for the implementation of the reactions below, and more particularly for the implementation of reactions at a temperature of less than or equal to 600° C. and preferably less than 500° C.

Reactions Implementable According to the Invention

The invention is advantageously implemented for the production of acrylic acid of renewable origin, more particularly the production of acrylic acid from glycerol, including a first step of dehydrating the glycerol to acrolein, followed by a step of gas-phase oxidation of the acrolein thus obtained; or in the production of acrylic acid by dehydration of 2-hydroxypropionic acid (lactic acid) or 3-hydroxypropionic acid and of their esters.

The invention allows in particular the implementation of a process for dehydrating glycerol to acrolein. In this type of process, the glycerol is fed in the form of an aqueous solution with a concentration of 20% to 95% by mass. The greater the concentration of the glycerol and the greater the tendency of the catalysts to form coke, the catalyst requires regular regeneration. According to the process described in patent application WO 2006/087083, the reaction is advantageously implemented in the presence of oxygen, since the addition of oxygen in the glycerol dehydration reaction allows the catalyst lifetime to be extended and the regenerating operations to be spaced further apart.

The reaction is typically carried out at a temperature of 220 to 350° C. and preferably of 280 to 320° C. and at a pressure ranging from atmospheric pressure to several bars (5, for example).

The catalysts which can be used for this reaction are acid catalysts, having in particular a Hammett acidity of less than +2, of the kind that are described, for example, in documents EP 1 848 681, WO 2009/12855, WO 2009/044081, or WO 2010/046227. Many acidic catalysts may be suitable for this reaction. They include phosphated zirconias, tungstated zirconias, siliceous zirconias, oxides of titanium or tin that are impregnated with tungstate or phosphotungstate or silicotungstate, phosphated aluminas or phosphated silicas, heteropolyacids or salts of heteropolyacids, iron phosphates, and iron phosphates including a promoter.

In the context of this process, the catalyst suffers deactivation in particular by coking. This deactivation may, however, be retarded by the injection of oxygen in situ in the reaction zone 3. The molar $O_2$/glycerol ratio at the reactor inlet is from 0.1 to 1.5 (preferably from 0.3 to 1.0) and the oxygen partial pressure is less than 7%.

The catalyst is regenerated in regeneration zone 4 by injection of oxygen.

The invention also allows the implementation of a process for dehydrating lactic acid or 3-hydroxypropionic acid (and their corresponding esters) to acrylic acid.

Lactic acid has a boiling point of around 217° C., and 3-hydroxypropionic acid has a boiling point of 279° C. (calculated value). The flammability limits for lactic acid in air are 3.1% (lower limit) and 18% (upper limit). The methyl ester of lactic acid has a boiling point of 145° C., for flammability limits of 1.1% and 3.6% (providing a greater flexibility of use than for the acid). The methyl ester of 3-hydroxypropionic acid has a boiling point of 179° C. (180° C. as calculated value). The ethyl ester of lactic acid has a boiling point of 154° C., and flammability limits of 1.6% and 10.6%. The ethyl ester of 3-hydroxypropionic acid has a boiling point of 187.5° C.

For these reactions, a reactor configuration is used which is substantially identical to that for the dehydration of glycerol. The dehydration conditions are a temperature of 220 to 400° C., and preferably of 250 to 350° C., and a pressure of 0.5 to 5 bar.

The catalysts which may be suitable for these reactions are acidic catalysts, having in particular a Hammett acidity of less than +2. The catalysts may be selected from natural or synthetic siliceous materials or the acidic zeolites; from inorganic supports, such as oxides, covered with inorganic acids or with mono-, di-, tri- or polyacids; from oxides or mixed oxides or else heteropolyacids or salts of heteropolyacids that contain in particular at least one element selected from the group consisting of W, Mo, and V. Among the mixed oxides, mention may be made particularly of those based on iron and on phosphorus and of those based on cesium, phosphorus, and tungsten.

Other catalysts which may also be suitable for these reactions are obtained from phosphates and/or sulfates of alkali metals, alkaline-earth metals, and rare earths, and mixtures thereof. This group thus includes lanthanum phosphates and oxyphosphates, sodium phosphates, calcium phosphates, calcium sulfate, magnesium sulfate, and the corresponding hydrogen phosphates, aluminum phosphate, boron phosphate. All of the abovementioned active materials may be impregnated or coated on any type of support such as: alumina, titanium oxide, zirconium oxide, silica, but also the corresponding mixed oxides, and silicon carbide.

The lactic or 3-hydroxypropionic acid partial pressure is generally from 1% to 10% and preferably from 2% to 6%.

Likewise in the context of these reactions, the catalyst suffers deactivation in particular by coking. This deactivation may be delayed by injecting oxygen in situ in the reaction zone 3. The conditions relating to the injection of oxygen are the same as those described above in connection with the dehydration of glycerol.

The regeneration is carried out by injection of oxygen, as described above in connection with the dehydration of glycerol.

The invention also enables implementation of a process for dehydrating 2-hydroxyisobutyric acid or 3-hydroxyisobutyric acid to methacrylic acid.

For this type of reaction, a reactor configuration is used which is substantially identical to that for the dehydration of glycerol. The dehydration conditions are a temperature of 200 to 400° C., and preferably of 250 to 350° C., and a pressure of 0.5 to 5 bar. The catalysts which may be suitable for this reaction are acidic catalysts, having in particular a Hammett acidity of less than +2. The catalysts may be selected from natural or synthetic siliceous materials or the acidic zeolites; from inorganic supports, such as oxides, covered with inorganic acids or with mono-, di-, tri- or polyacids; from oxides or mixed oxides or else heteropolyacids or salts of heteropolyacids that contain in particular at least one element selected from the group consisting of W, Mo, and V. Among the mixed oxides, mention may be made particularly of those based on iron and on phosphorus and of those based on cesium, phosphorus, and tungsten.

Catalysts which may also be suitable for this reaction are obtained from phosphates and/or sulfates of alkali metals, alkaline-earth metals, and rare earths, and mixtures thereof. This group thus includes lanthanum phosphates and oxyphosphates, sodium phosphates, calcium phosphates, calcium sulfate, magnesium sulfate, and the corresponding hydrogen phosphates, aluminum phosphate, boron phosphate. All of the abovementioned active materials may be impregnated or coated on any type of support such as: alumina, titanium oxide, zirconium oxide, silica, but also the corresponding mixed oxides, and silicon carbide.

The (2- or 3-)hydroxyisobutyric acid partial pressure is generally from 1% to 20% and preferably from 2% to 10%.

Likewise in the context of these reactions, the catalyst suffers deactivation in particular by coking. This deactivation may be delayed by injecting oxygen in the reaction zone 3. The conditions relating to the injection of oxygen are the same as those described above in connection with the dehydration of glycerol.

The regeneration is carried out by injection of oxygen, as described above in connection with the dehydration of glycerol.

The invention also enables implementation of selective oxidations such as the oxidation of methanol to formaldehyde or to dimethoxymethane; the oxidation of ethanol to acetaldehyde or to diethoxyethane; the oxidation of ortho-xylene or naphthalene to phthalic anhydride, and the oxidation of benzene, butene, butanol, or butane to maleic anhydride.

For these oxidation reactions, the deactivation of the catalyst by coking takes place relatively slowly, but there is also a phenomenon of deactivation by sublimation of metal oxides. The use of a fluidized bed according to the invention allows the catalyst to be turned in order to make the surroundings uniform and to limit the incidence of hot spots, a fact which is particularly advantageous relative to a fixed bed.

In the case of the reactions for oxidation of methanol to formaldehyde or dimethoxymethane, and for oxidation of ethanol to acetaldehyde or diethoxyethane, the catalysts which may be suitable are mixed oxides, such as iron molybdenum oxides or molybdenum oxides containing metals selected from bismuth, vanadium, tungsten, copper, nickel, and cobalt. The operating conditions are a temperature of between 200 and 350° C., preferably between 250 and 300° C., and a pressure of between 1 and 5 bar. The alcohol partial pressure may vary within a wide range from 3% to 50%, and preferably from 5% to 40%, depending on the type of product desired. Where the aldehydes are the desired products, the alcohol partial pressure is between 3% and 10% and preferably between 5% and 9%. Where the acetals are the desired products, the alcohol partial pressure is between 10% and 50% and preferably between 20% and 40%.

In the case of the reactions for oxidizing ortho-xylene and naphthalene to phthalic anhydride, the catalysts selected preferably contain vanadium, and preferably supported vanadium oxide. The operating conditions are a pressure of 1 to 5 bar and reaction temperatures of 280 to 450° C.

In the case of the reactions for oxidation of butane, butenes, butanol, and benzene to maleic anhydride, the catalysts which are suitable contain vanadium, in the form of supported vanadium oxide or in the form of supported mixed vanadium-phosphorus oxide. The temperatures of the reactions are from 350 to 500° C. and the pressures are from 1 to 5 bar.

In the case of the reactions for oxidation of propylene to acrolein, of isobutene or of tert-butanol to methacrolein, the catalysts which are suitable consist primarily of molybdenum, and contain elements selected from (but not exclusively) the following elements: nickel, iron, cobalt, tungsten, potassium, bismuth, antimony, chromium. The reaction temperatures are between 320 and 450° C. The total pressures are between 1 and 5 bar. The hydrocarbon compound partial pressures are between 5% and 15%, and the $O_2$/hydrocarbon compound ratio at the reactor inlet is between 0.5 and 4, and preferably between 0.8 and 2, and more preferably between 1 and 1.8, and more preferably still between 1.2 and 1.6.

In the case of the reactions for oxidation of acrolein to acrylic acid, and of methacrolein to methacrylic acid, the catalysts which are suitable consist primarily of molybdenum, and contain elements selected from the following elements (but not exclusively): vanadium, tungsten, copper, antimony, niobium, strontium, phosphorus, iron. The operating temperatures are between 250 and 350° C., for a total pressure of 1 to 5 bar. The aldehyde partial pressure is between 5% and 15%, and the $O_2$/aldehyde ratio at the reactor inlet is between 0.3 and 1.2, and preferably between 0.5 and 1.

Other oxidation reactions which can be implemented according to the invention are as follows:

The production of acrylic acid from propylene and oxygen, the co-products being acrolein, acetic acid, maleic acid, propionic acid, acetaldehyde, and acetone, for example at a temperature of 300 to 400° C. and at a pressure of 1 to 3 bar.

The production of ethylene oxide from ethylene and oxygen, the co-products being acetaldehyde and formaldehyde, for example at a temperature of 230 to 290° C. and at a pressure of 10 to 30 bar.

The production of 1,2-dichloroethane from ethylene, hydrochloric acid, and oxygen, the co-products being carbon monoxide, chloral, and various chlorinated compounds, for example at a temperature of 220 to 300° C. and at a pressure of 2 to 6 bar.

The production of terephthalic acid from p-xylene and oxygen, the co-products being maleic anhydride, o-toluic acid, and benzoic acid, for example at a temperature of 175 to 230° C. and at a pressure of 15 to 30 bar.

The reactor according to the invention may also be suitable for ammoxidation reactions involving ammonia/oxygen/inert/hydrocarbon compound mixtures. The hydrocarbon compounds that may be used include propylene, isobutene, acrolein, methacrolein, but also aromatic compounds. The ammoxidation reactions are performed at a temperature of 50 to 100° C. higher than the corresponding oxidation temperatures.

As an example, acrylonitrile can be produced (with co-production of acetonitrile, hydrocyanic acid, and carbon monoxide) from propylene and/or propane, oxygen, and ammonia, for example at a temperature of 400 to 500° C. and at a pressure of 1 to 4 bar.

The invention claimed is:

1. A chemical reaction process comprising concomitantly:
   feeding by a reaction stream of a fluidized bed of catalyst particles into a reaction zone disposed in a chamber of a reactor,
   withdrawing a stream comprising reaction products at an outlet of the reaction zone,
   passing, using separating means, the catalyst particles of the fluidized bed from the reaction zone to a regeneration zone disposed inside the chamber of the reactor,
   feeding the regeneration zone by a regeneration stream,
   regenerating the catalyst particles and pneumatically entraining the catalyst particles into the regeneration zone,
   withdrawing an exhaust gas at the outlet of the regeneration zone, and
   returning the entrained catalyst particles to the reaction zone;
   wherein the deactivation time of the catalyst is from 1 to 20 times greater than regeneration time, the deactivation time being a time when the catalyst particles lose 25% of their initial efficiency and the regeneration time being a time from the deactivation time until the catalyst particles regain up to about 100% of said initial efficiency; wherein the separation means comprises a tubular wall and wherein the reaction zone is disposed outside the tubular wall and the regeneration zone is disposed inside the tubular wall.

2. The process as claimed in claim 1, wherein the stream of catalyst particles from the reaction zone to the regeneration zone is regulated by the injection of a backpressure gas.

3. The process as claimed in claim 1, wherein the regeneration stream comprises oxygen.

4. The process as claimed in claim 1, which is:
   a process for dehydrating glycerol to acrolein; or
   a process for dehydrating lactic acid to acrylic acid; or
   a process for dehydrating 3-hydroxypropionic acid to acrylic acid;
   a process for dehydrating 3-hydroxyisobutyric acid to methacrylic acid; or
   a process for dehydrating 2-hydroxyisobutyric acid to methacrylic acid; or
   a process for selective oxidation such as the oxidation of methanol to formaldehyde or dimethoxymethane; the oxidation of ethanol to acetaldehyde or to diethoxyethane; the oxidation of ortho-xylene or naphthalene to phthalic anhydride, or the oxidation of benzene, butene, butanol, or butane to maleic anhydride;
   a process for oxidizing propylene to acrolein, and isobutene or tert-butanol to methacrolein; or
   a process for oxidizing acrolein to acrylic acid, and methacrolein to methacrylic acid.

5. The process as claimed in claim 3, wherein the reaction stream comprises oxygen.

* * * * *